(12) United States Patent  
Palanker et al.

(10) Patent No.: US 7,357,802 B2  
(45) Date of Patent: Apr. 15, 2008

(54) ELECTROSURGICAL SYSTEM WITH UNIFORMLY ENHANCED ELECTRIC FIELD AND MINIMAL COLLATERAL DAMAGE

(75) Inventors: Daniel V. Palanker, Sunnyvale, CA (US); Alexander Vankov, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 170 days.

(21) Appl. No.: 10/779,529

(22) Filed: Feb. 13, 2004

(65) Prior Publication Data

US 2004/0236321 A1 Nov. 25, 2004

Related U.S. Application Data

(60) Provisional application No. 60/447,715, filed on Feb. 14, 2003.

(51) Int. Cl.
*A61B 18/18* (2006.01)
(52) U.S. Cl. ....................................................... 606/45
(58) Field of Classification Search ............. 606/27–52
See application file for complete search history.

(56) References Cited

U.S. PATENT DOCUMENTS

| | | | |
|---|---|---|---|
| 3,799,168 A | 3/1974 | Peters | |
| 3,903,891 A | 9/1975 | Brayshaw | 128/303.14 |
| 3,970,088 A | 7/1976 | Morrison | |
| 3,987,795 A | 10/1976 | Morrison | |
| 4,043,342 A | 8/1977 | Morrison, Jr. | |
| 4,074,718 A | 2/1978 | Morrison, Jr. | |
| 4,161,950 A | 7/1979 | Doss et al. | |
| 4,202,337 A | 5/1980 | Hren et al. | 128/303.14 |
| 4,228,800 A | 10/1980 | Degler, Jr. et al. | 128/303.14 |
| 4,248,231 A | 2/1981 | Herczog et al. | |
| 4,429,694 A | 2/1984 | McGreevy | |
| 4,476,862 A | 10/1984 | Pao | 128/303.17 |
| 4,534,347 A | 8/1985 | Taylor | |
| 4,559,943 A | 12/1985 | Bowers | |
| 4,589,411 A | 5/1986 | Friedman | |
| 4,590,934 A * | 5/1986 | Malis et al. | 606/37 |
| 4,593,691 A | 6/1986 | Lindstrom et al. | 128/303.14 |
| 4,597,388 A | 7/1986 | Koziol et al. | 128/303.1 |
| 4,655,215 A | 4/1987 | Pike | |
| 4,674,499 A | 6/1987 | Pao | 128/303.14 |
| 4,781,175 A | 11/1988 | McGreevy et al. | 128/303.17 |
| 4,805,616 A | 2/1989 | Pao | |
| 4,901,709 A | 2/1990 | Rattner | 128/24 |
| 4,927,420 A | 5/1990 | Newkirk et al. | |

(Continued)

Primary Examiner—Roy D. Gibson
Assistant Examiner—Pete Vrettakos
(74) *Attorney, Agent, or Firm*—Morrison & Foerster LLP

(57) ABSTRACT

The present invention is directed towards an electrosurgical cutting system. The system comprises an electrically conductive blade, having first and second blade surfaces. First and second insulators are affixed to the first and second blade surfaces, respectively. A blade edge, a region between the first and second blade surfaces, has an edge radius of curvature, which preferably is small. A source of pulsed electrical energy coupled to the electrically conductive blade provides a substantially uniform and highly enhanced electric field along a cutting portion of the blade edge.

The system can also be comprised of a wire electrode. Despite the fact that its field is strongly enhanced around the apex, a uniform vapor cavity is formed and then ionized using an appropriately designed burst of pulses, preferably of alternating polarity.

29 Claims, 10 Drawing Sheets

U.S. PATENT DOCUMENTS

| | | | |
|---|---|---|---|
| 4,936,301 A | 6/1990 | Rexroth et al. | 606/45 |
| 4,943,290 A | 7/1990 | Rexroth et al. | 606/45 |
| 5,080,660 A | 1/1992 | Buelna | |
| 5,088,997 A | 2/1992 | Delahuerga et al. | 606/42 |
| 5,108,391 A | 4/1992 | Flachenecker et al. | 606/38 |
| 5,217,457 A | 6/1993 | Delahuerga et al. | 606/42 |
| 5,254,121 A | 10/1993 | Manevitz et al. | 606/128 |
| 5,267,994 A | 12/1993 | Gentelia et al. | |
| 5,281,216 A | 1/1994 | Klicek | 606/42 |
| 5,300,068 A | 4/1994 | Rosar et al. | 606/34 |
| 5,318,563 A * | 6/1994 | Malis et al. | 606/38 |
| 5,454,809 A | 10/1995 | Janssen | |
| 5,549,604 A | 8/1996 | Sutcu et al. | |
| 5,569,242 A | 10/1996 | Lax et al. | 606/42 |
| 5,658,279 A | 8/1997 | Nardella et al. | 606/45 |
| 5,669,904 A | 9/1997 | Platt, Jr. et al. | 606/27 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,909 A | 12/1997 | Eggers et al. | 604/114 |
| 5,700,262 A | 12/1997 | Acosta et al. | 606/48 |
| 5,766,153 A | 6/1998 | Eggers et al. | 604/114 |
| 5,785,704 A | 7/1998 | Bille et al. | 606/17 |
| 5,843,019 A | 12/1998 | Eggers et al. | 604/22 |
| 5,860,976 A | 1/1999 | Billings et al. | 606/45 |
| 5,873,855 A | 2/1999 | Eggers et al. | 604/114 |
| 5,891,095 A | 4/1999 | Eggers et al. | 604/114 |
| 5,958,266 A | 9/1999 | Fugo et al. | 219/121.59 |
| 6,004,319 A | 12/1999 | Goble et al. | |
| 6,032,674 A | 3/2000 | Eggers et al. | 128/898 |
| 6,047,700 A | 4/2000 | Eggers et al. | 128/898 |
| 6,056,746 A | 5/2000 | Goble et al. | |
| 6,066,134 A | 5/2000 | Eggers et al. | 606/32 |
| 6,066,137 A | 5/2000 | Greep | |
| 6,102,046 A | 8/2000 | Weinstein et al. | 128/898 |
| 6,113,594 A | 9/2000 | Savage | 606/41 |
| 6,132,427 A | 10/2000 | Jones et al. | |
| 6,135,998 A | 10/2000 | Palanker | 606/39 |
| 6,149,620 A | 11/2000 | Baker et al. | 604/22 |
| 6,149,646 A | 11/2000 | West, Jr. et al. | |
| 6,174,309 B1 | 1/2001 | Wrublewski et al. | 606/45 |
| 6,210,404 B1 | 4/2001 | Shadduck | |
| 6,228,082 B1 | 5/2001 | Baker et al. | 606/49 |
| 6,254,600 B1 | 7/2001 | Willink et al. | 606/41 |
| 6,267,757 B1 | 7/2001 | Aita et al. | 606/33 |
| 6,287,305 B1 | 9/2001 | Heim et al. | |
| 6,287,306 B1 | 9/2001 | Kroll et al. | 606/41 |
| 6,352,535 B1 | 3/2002 | Lewis et al. | 606/45 |
| 6,355,032 B1 | 3/2002 | Hovda et al. | 606/32 |
| 6,364,877 B1 | 4/2002 | Goble et al. | 606/34 |
| 6,447,511 B1 | 9/2002 | Slater | 606/48 |
| 6,458,121 B1 * | 10/2002 | Rosenstock et al. | 606/34 |
| 6,478,794 B1 | 11/2002 | Trapp et al. | 606/45 |
| 6,479,785 B1 | 11/2002 | Fugo et al. | |
| 6,533,781 B2 * | 3/2003 | Heim et al. | 606/45 |
| 6,620,160 B2 | 9/2003 | Lewis et al. | |
| 6,770,071 B2 | 8/2004 | Woloszko et al. | |
| 6,780,178 B2 | 8/2004 | Palanker et al. | |
| 6,787,730 B2 | 9/2004 | Coccio et al. | |
| 6,837,887 B2 | 1/2005 | Woloszko et al. | |
| 7,238,185 B2 | 7/2007 | Palanker et al. | |
| 2003/0097129 A1 | 5/2003 | Davison et al. | |
| 2004/0267254 A1 | 12/2004 | Manzo et al. | |
| 2005/0043728 A1 | 2/2005 | Ciarrocca | |
| 2005/0143726 A1 | 6/2005 | Bortkiewicz | |
| 2005/0220674 A1 | 10/2005 | Shafirstein et al. | |
| 2005/0234446 A1 | 10/2005 | Van Wyk et al. | |
| 2006/0069386 A1 | 3/2006 | Dubnack et al. | |
| 2006/0259033 A1 | 11/2006 | Nesbitt | |

* cited by examiner

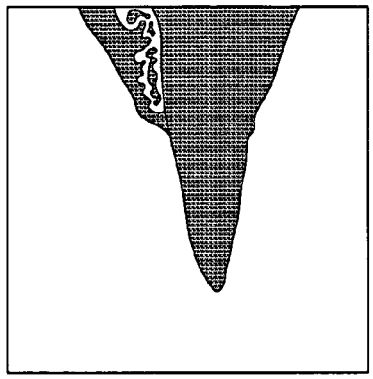
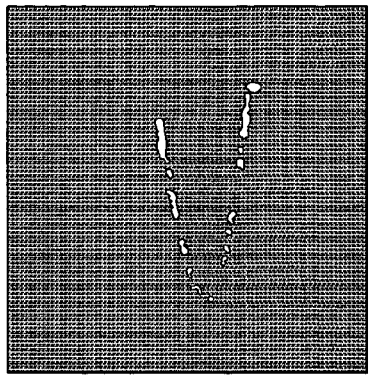
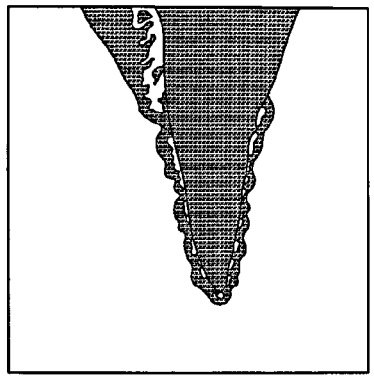
Fig. 5a      Fig. 5b      Fig. 5c
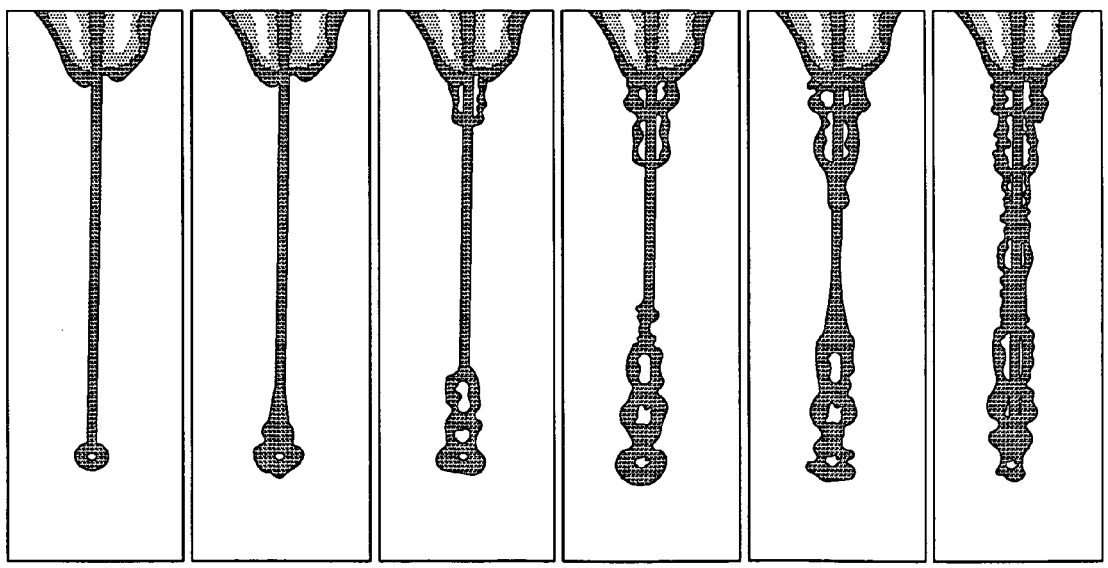
Fig. 6

ELECTROSURGICAL SYSTEM WITH UNIFORMLY ENHANCED ELECTRIC FIELD AND MINIMAL COLLATERAL DAMAGE

CROSS REFERENCE TO RELATED APPLICATIONS

This application is related to and claims priority from U.S. provisional application 60/447,715, filed on Feb. 14, 2003, and hereby incorporated by reference.

GOVERNMENT SPONSORSHIP

The present invention was made with support from the National Institutes of Health, under contract number R01-EY-12888. The government has certain rights in this invention.

FIELD OF THE INVENTION

The present invention relates generally to an electrosurgical device, and in particular, to the design of efficient electro-surgical probes and waveforms for pulsed plasma-mediated cutting, fragmentation, and evaporation of biological tissue in fluid media.

BACKGROUND

Plasma-mediated cutting of soft biological tissue in conductive liquid media with sub-microsecond pulses of high voltage is described in the patent of Palanker [U.S. Pat. No. 6,135,998]. Dissection of tissue based on explosive vaporization by short (under few microseconds) pulses of high voltage is described in the patent of Lewis et al. [U.S. Pat. No. 6,352,535]. In these applications an inlaid cylindrical electrode (i.e. a wire embedded into a thick insulator and exposed at its end) is applied to ionize, evaporate and fragment tissue in proximity of electrode using dielectric breakdown or vaporization of water induced by a high electric field. An inlaid cylindrical electrode cannot penetrate into tissue and thus can only produce shallow cuts on its surface. Due to the pulsed regime of application, this device produces a series of perforations in tissue, which often do not merge into a continuous cut. In addition, cavitation bubbles accompanying each pulse create substantial collateral damage in tissue during their growth and collapse phases [Effect of the Probe Geometry on Dynamics of Cavitation, D. Palanker, A. Vankov, and J. Miller, *Laser-Tissue Interactions XIII*, vol. 4617 SPIE (2002)]. The size of such a damage zone typically far exceeds the size of the electrode and the corresponding zone of initial energy deposition [Effect of the Probe Geometry on Dynamics of Cavitation, D. Palanker, A. Vankov, and J. Miller, *Laser-Tissue Interactions XIII*, vol. 4617 SPIE (2002)]. Reduction in pulse energy helps to reduce the mechanical damage, but also leads to decreased cutting depth.

A second mechanism of electrosurgical ablation is vaporization of tissue in the proximity of the probe by overheating a conductive medium with either a continuous radio frequency waveform or with sub-millisecond long bursts of pulses. This mechanism is universally applicable to soft and hard biological tissue ranging from membranes and retina to skin and cartilage. In such regimes wire electrodes are typically used, although the use of a device that could provide a uniform electric field along its length would be preferable.

Without considering end effects, the electric field in a conductive liquid at distance r from a cylindrical electrode with potential U and radius $r_0$ much smaller than its length L is:

$$E = U/(r \ln(r_0/L)), \quad (1)$$

assuming that the return electrode is much larger and positioned at infinity. The threshold electric field required for dielectric breakdown in water is on the order of $10^5$-$10^6$ V/cm [Jones, H. M. & Kunhardt, E. E. Development of Pulsed Dielectric Breakdown In Liquids. *Journal of Physics D-Applied Physics* 28, 178-188 (1995); Jones, H. M. & Kunhardt, E. E. Pulsed Dielectric Breakdown of Pressurized Water and Salt Solutions. *Journal of Applied Physics* 77, 795-805 (1995)]. Such a threshold electric field $E_{th}$ can be achieved with electric pulses of several kV on a wire electrode with a diameter of several tens of micrometers. The threshold voltage required for ionization of a surface layer of water is:

$$U_{th} = E_{th} r_0 \ln(L/r_0). \quad (2)$$

The corresponding threshold energy is:

$$F_{th} = 2\pi E_{th}^2 r_0^2 L \ln(L/r_0). \quad (3)$$

Evaporation of water in the proximity of an electrode begins when the temperature is elevated above 100° C. The threshold voltage required for vaporization of a surface layer is:

$$U_{th} = (c\rho\Delta T/(\tau\gamma))^{1/2} r_0 \ln(L/r_0) \quad (4)$$

where $\tau$ is a pulse duration, $\gamma$ is the electrical conductivity of the liquid, $\rho$ is the liquid density, c is the liquid heat capacity, and $\Delta T$ is the temperature change. The corresponding threshold energy is:

$$F_{th} = 2\pi c\rho\Delta T r_0^2 L \ln(L/r_0). \quad (5)$$

Lower threshold voltage and energy, as well as better localization of energy deposition can be achieved by decreasing the radius of electrode $r_0$, as follows from equations 1-5. However, this approach is limited by the mechanical strength of the thin wire and its visibility. In addition, the problem of non-uniform distribution of electric field along the electrode, and particularly, enhancement at the apex remains.

This enhancement is illustrated in FIG. 1A, which shows the electric field surrounding a wire electrode. The field is stronger at the apex (i.e., at distance=0) and is weaker in its cylindrical portion. Thus ionization and vaporization on such an electrode will always begin and be dominant at locations of enhanced field strength, leading to uneven cutting and excessive damage in front of these singular points, as shown in FIG. 2.

One geometry that provides uniform enhancement of an electric field is a ring electrode shown in FIG. 3. Its field is uniform except for the points of deviation from perfectly round shape, such as where the ring electrode contacts with a holder. Fortunately, these regions of deviation can be kept away from tissue during surgery. The threshold voltage on such an electrode is set by the wire radius (equations 2 and 4) and thus is limited by the mechanical strength of the wire. For example, a thin wire is very weak and flexible and is thus inapplicable to manipulation of tissue. In addition, wires thinner than 25 microns are barely seen under a conventional surgical microscope, and this makes their use even more difficult. An additional problem with the application of thin wires is that erosion of thin wires greatly limits their lifetime.

Below we describe probe geometry and pulse waveform structures that provide solutions to these and other problems.

SUMMARY

What is desired is a penetrating electrode that can cut tissue uniformly along an extensive cutting zone, rather than just with its apex. As will be shown below, this objective can be achieved through geometric tailoring of the electrode, careful design of the electrical pulses applied to the electrode, or a combination of these approaches.

Tissue can be cut uniformly along an extensive cutting zone through the use of an electrosurgical cutting system that comprises an electrically conductive blade, insulators, and a source of pulsed electrical energy coupled to the blade. In particular, the blade has a first blade surface, a second blade surface, and a blade thickness. The blade thickness is the smallest local distance between the first blade surface and the second blade surface. First and second insulators are affixed to the first and second blade surfaces, respectively. The first blade surface and the second blade surface come together along a blade edge. Ideally, the blade edge is perfectly sharp, but in practice the blade edge will be somewhat rounded and it is this rounded region between the first and second blade surfaces that will be called the blade edge. The blade edge will have an edge radius of curvature, which ideally will be small (thereby providing a sharp blade edge). In practice, the entire blade edge is unlikely to be used for cutting, but only a blade cutting portion, which is a predetermined length of the blade that is used for cutting biological tissue. Unlike the ring electrode discussed earlier, the use of a blade provides substantial mechanical strength while the use of a blade edge with a small edge radius of curvature can provide a substantially uniform enhanced electric field along its cutting zone.

In preferred embodiments, biological tissue is cut with the electrosurgical system with a sharp blade edge by manipulating the blade in a biological medium such that the sharp blade edge is in close proximity to the tissue to be cut. The approach then involves applying at least one electrical pulse along the cutting zone of the blade edge that contacts the region of biological tissue to be cut. In preferred embodiments, multiple electrical pulses are applied to the sharp blade edge. The electrical pulses are of sufficient strength to generate electric breakdown in the tissue that is in a close proximity to the sharp blade edge. The pulse duration is sufficiently long for the generation of a streamer and spark discharge but is sufficiently short to avoid the development of a high current arc discharge. In this case, whether the current was high would be with comparison to the current generated in the biological medium prior to the development of the arc.

Tissue can also be cut uniformly along an extensive cutting zone without the use of a blade as described above. In this approach, biological tissue immersed in a liquid medium can be cut uniformly along a cutting zone of an electrode (not necessarily in the form of a blade) by first forming a uniform vapor cavity surrounding the cutting zone of the electrode. This can be accomplished through the tailoring of the electrical pulses applied to the electrode. After forming the uniform vapor cavity, this approach involves ionizing the vapor in the cavity. This results in a plasma-mediated discharge into the biological tissue inside the vapor cavity.

These two approaches can be combined to form very effective methods for cutting biological tissue. In the combined approach for cutting biological tissue, a burst of pulsed electrical energy is applied to a blade having a blade edge with a relatively small edge radius of curvature. The number of pulses and the energy of each pulse is chosen such that liquid adjacent to the blade cutting portion of the blade edge prior to application of the burst of pulses is, at some time prior to completion of the burst of pulses, vaporized along the entire blade cutting portion of the blade edge. With the combined approach, nonuniformities in the electric field along the blade edge are effectively smoothed out.

In the most preferred embodiments of these methods, the electrical pulses have alternating polarity. Alternating the polarity of the pulses greatly reduces the electroporation-related tissue damage away from the immediate vicinity of the cut.

An electrosurgical cutting system as described above can be readily fabricated. A blade of an electrically conductive material is provided. The blade will have a first blade surface and an opposing second blade surface. The first and second blade surfaces join at a blade edge. In preferred embodiments, the first and second blade surfaces in a predetermined cutting zone near the blade edge are tapered to form a tapering region, which is the region in which the first and second blade surfaces converge towards each other. The blade is coated with a thin layer of insulator to form a coated blade. The coated blade is immersed in a conductive medium. A source of pulsed electrical energy is coupled to the blade. Pulsed electrical energy is then applied to the blade until the thin layer of insulator is removed from the vicinity of the blade edge. Preferably the thin layer of insulator is removed over the entire tapering region.

BRIEF DESCRIPTION OF THE DRAWINGS

FIG. 5A shows a blade electrode with insulated flat sides and an exposed sharp edge and tapering region on a perimeter. FIG. 5B shows light emission by plasma forming on the exposed portion after a 200 ns pulse of 3.4 kV in saline. FIG. 5C shows vapor (cavitation) bubbles uniformly covering the exposed portion 5 μs after the pulse.

FIG. 6 shows a sequence of photographs demonstrating formation of a uniform cavity along an electrode with a non-uniform electric field using a sequence (burst) of pulses.

For complete coverage of the electrode the duration of the burst should not exceed the lifetime of the first bubble

FIG. 8A shows the electrode before the vapor cavity formation. FIG. 8B shows a vapor cavity forming over the portion of the electrode not covered by the insulator. When the electrical potential is high enough, an electric discharge occurs between the electrode and the tissue as shown in FIG. 8C. As shown in FIG. 8C, the discharge is concentrated in the region of smallest separation (least resistance) between the electrode and the tissue.

DETAILED DESCRIPTION

Figure 4A:
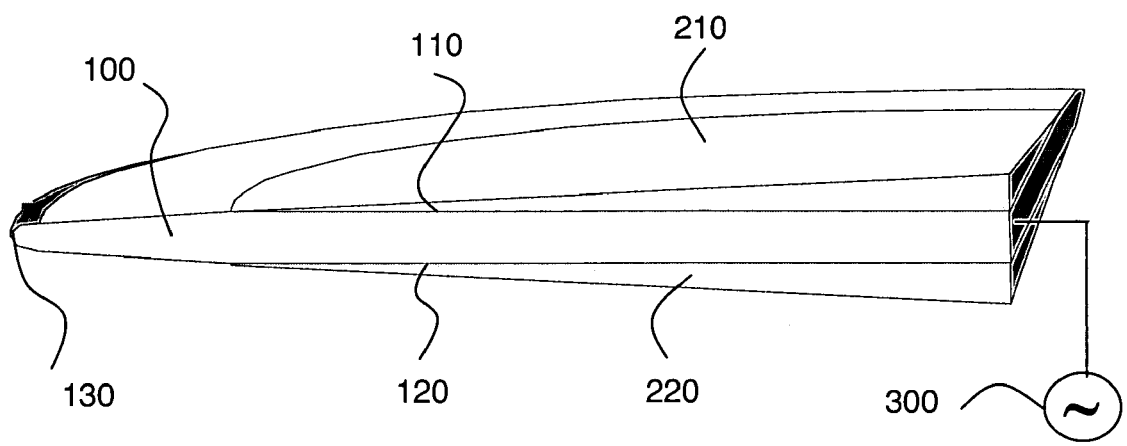
FIG. 4A shows an electrically conductive blade with insulators adjacent to the blade surfaces. The blade surfaces join at a blade edge.

Referring now to the drawings, where similar elements are numbered the same, FIG. 4A depicts an electrically conductive blade 100 having a first blade surface 110, a second blade surface 120, and a blade edge 130. In practice, the blade edge 130 is somewhat rounded, the edge radius of curvature 140 being shown in the magnified view of FIG. 4B. A first insulator 210 is affixed to the first blade surface 110. Similarly, a second insulator 220 is affixed to the second blade surface 120. To complete an electrosurgical cutting system, a source of pulsed electrical energy 300 is coupled to the blade 100. The other terminal from the source of pulsed electrical energy 300 is connected to a return electrode (not shown) immersed in the medium in which the blade 100 is inserted.

At any position on the blade 100, the blade thickness is the smallest distance between the first blade surface 110 and the second blade surface 120. In preferred embodiments, in the region adjacent the blade edge 130, the blade thickness is reduced approximately linearly as the first 110 and second 120 blade surfaces approach the blade edge 130. A blade tapering angle 150 is the angle of convergence of the first 110 and second 120 blade surfaces as the blade edge 130 is approached. In preferred embodiments the blade tapering angle 150 is less than 45 degrees; in more preferred embodiments the blade tapering angle 150 is less than 30 degrees; and in the most preferred embodiments the blade tapering angle 150 is less than 15 degrees.

Figure 4B:
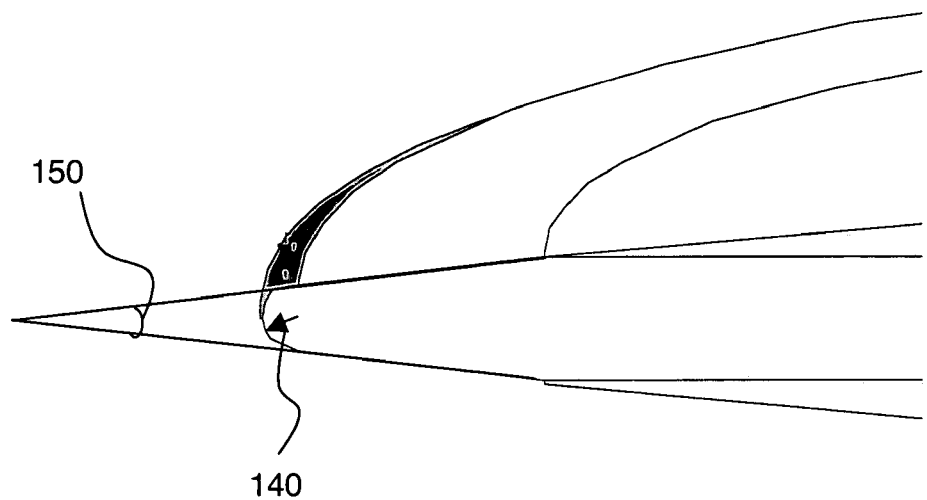
FIG. 4B shows a magnified view of the region around the blade edge. The blade tapering angle and the edge radius of curvature are shown.

Although in some embodiments the first 210 and second 220 insulators extend completely to the blade edge 130, in preferred embodiments the first 210 and second 220 insulators terminate prior to the blade edge 130. This leaves an exposed portion of the blade 100. As shown in FIGS. 4A and 4B, in the most preferred embodiments the exposed portion of the blade 100 extends through all or most of the tapering region. The exposed portion of the blade 100 between the blade edge 130 and the first 210 and second 220 insulators does not significantly reduce the electric field on the blade edge 130, but it decreases electrical impedance and thus increases the energy deposited into the biological tissue. Ending the first 210 and second 220 insulators some distance from the blade edge 130 keeps the insulators away from stresses induced by pulsed heating, vaporization and ionization. The extra distance also provides for some depth of metal for etching, which helps to increase the productive lifetime of the blade 100.

Figure 4C:
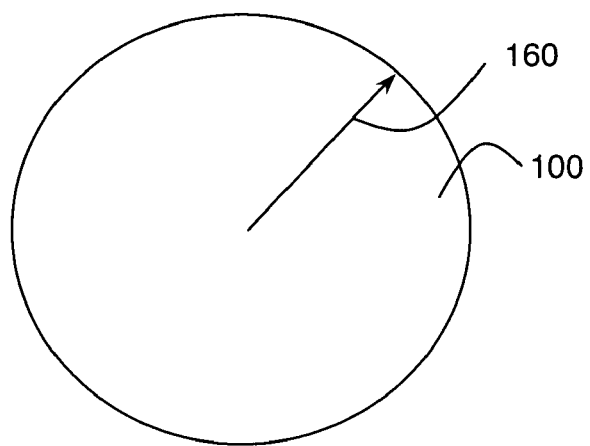
FIG. 4C shows a blade having a circular planform.
Figure 4D:
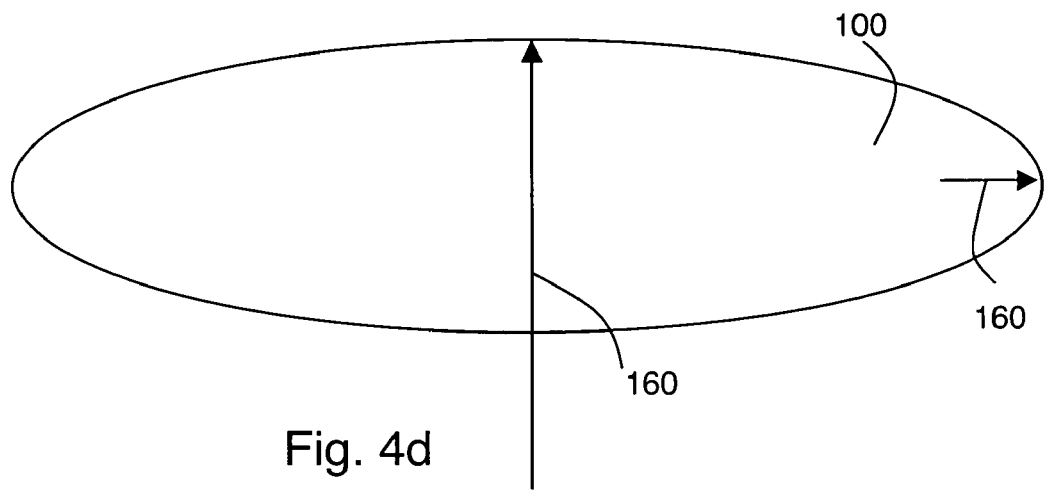
FIG. 4D shows a blade with an elliptical planform.
Figure 4E:
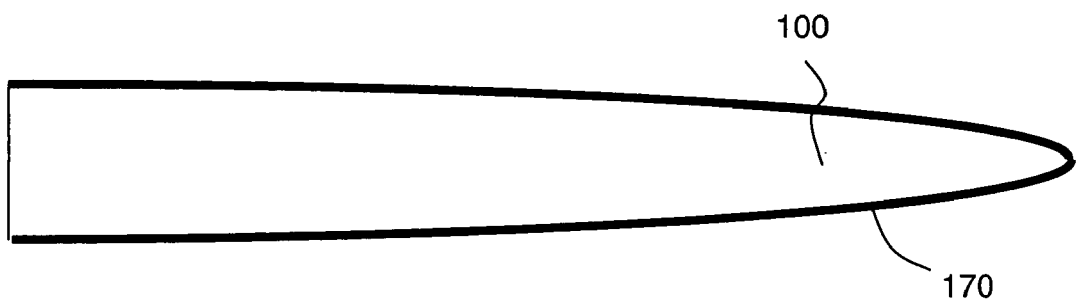
FIG. 4E shows a blade having a planform of more general shape, with the heavier line weight corresponding to the blade cutting portion.

FIGS. 4C-E show a variety of planform, or in-plane, shapes that are useful in various embodiments of the blade 100. In a canonical embodiment shown in FIG. 4C, the blade 100 takes the form of a disk, and hence the blade 100 is sometimes denoted a disk electrode. In such a blade 100, the first and second blade surfaces each has a radius of curvature in a plane perpendicular to the thickness, (sometimes known as the planar or in-plane radius of curvature 160) that is constant at all points on the blade 100. In another canonical embodiment shown in FIG. 4D, the blade 100 has an elliptical planform and the planar radius of curvature 160 (shown only schematically) varies considerably along the blade edge.

The planform shown in FIG. 4E is more general. In preferred embodiments the planar radius of curvature 160 is much larger than the edge radius of curvature, at least in the blade cutting portion 170. The blade cutting portion 170 is a predetermined length of the blade 100 that is used for cutting biological tissue. In FIG. 4E, the blade cutting portion 170 has been chosen to coincide with the heavier line. In preferred embodiments the planar radius of curvature 160 in the blade cutting portion 170 is at least 5, 10, 25, 50, 100, or even thousands of times greater than the edge radius of curvature. Regions where the planar radius of curvature 160 is much greater than the edge radius of curvature are considered to have a sharp blade edge. Having an extensive blade cutting portion 170 with a sharp blade edge facilitates uniform (or nearly uniform) enhancement of the electric field along the blade edge of the blade cutting portion 170.

Electrode with Uniformly Enhanced Field for Dielectric Breakdown in Liquid

Figure 1A:
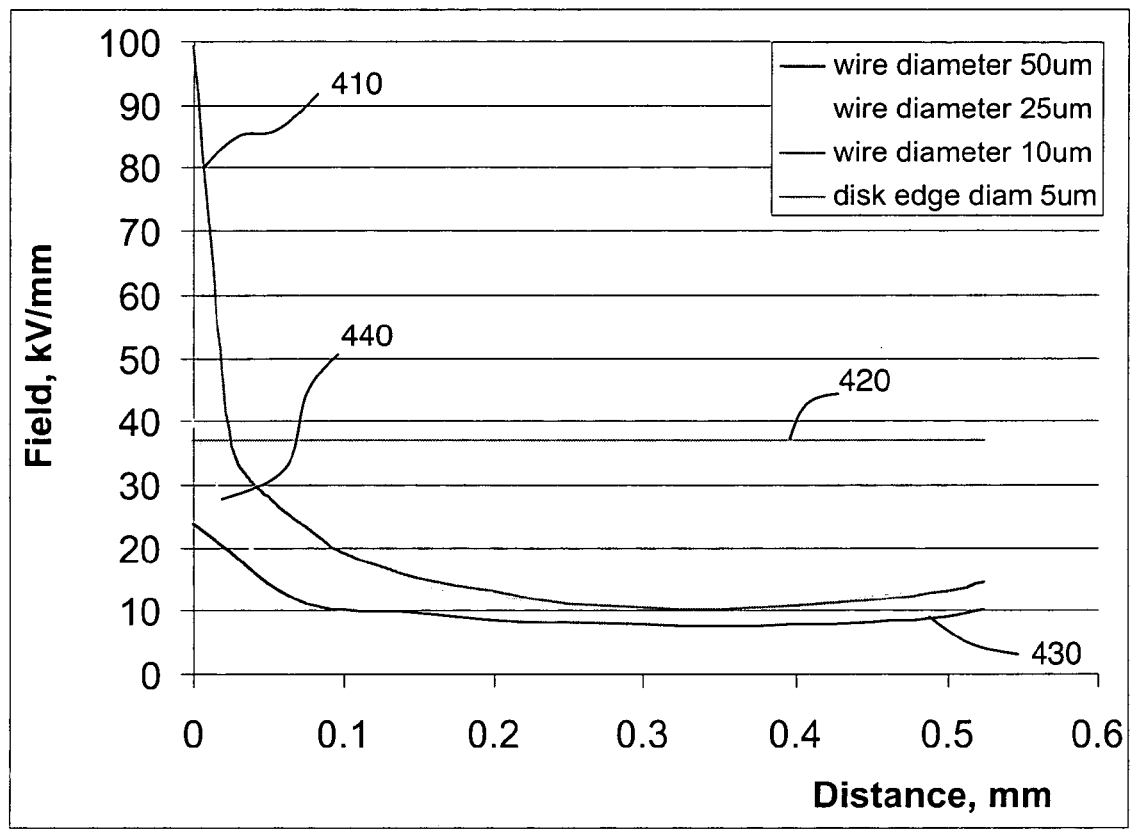
FIG. 1A illustrates the electric field along wire electrodes of 10, 25 and 50 microns in diameter (410, 440, and 430 respectively) and 530 microns in length, and along the 5 μm-thick edge of a disk electrode of 400 μm in diameter (420). The exposed zone of the disk electrode is 50 μm from the edge. The electrode potential is 600 V in all cases.
Figure 1B:
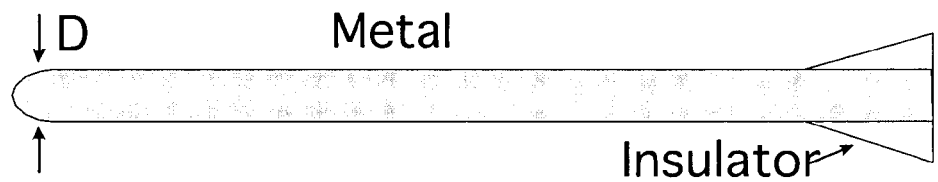
FIG. 1B illustrates the edge of the disk electrode used in FIG. 1A.
Figure 2:
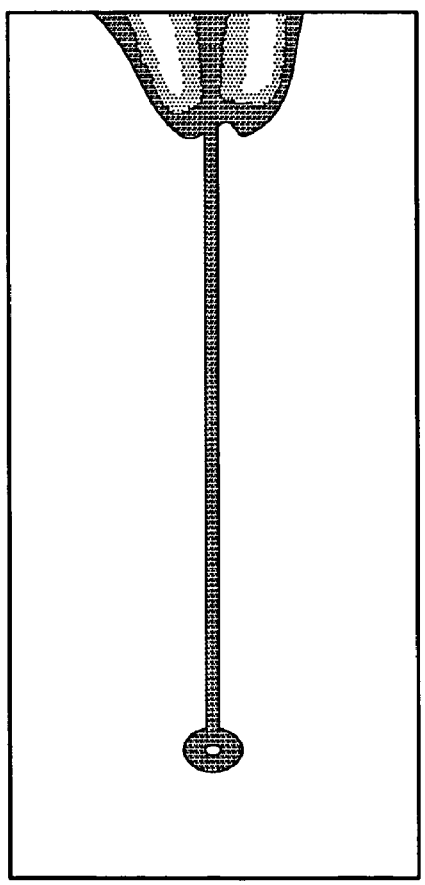
FIG. 2 shows the formation of a cavitation (vapor) cavity at the apex of the wire electrode in saline several microseconds after beginning of electrical pulse. This effect demonstrates that electric field at the apex is much higher than in other parts of the wire electrode.
Figure 3:
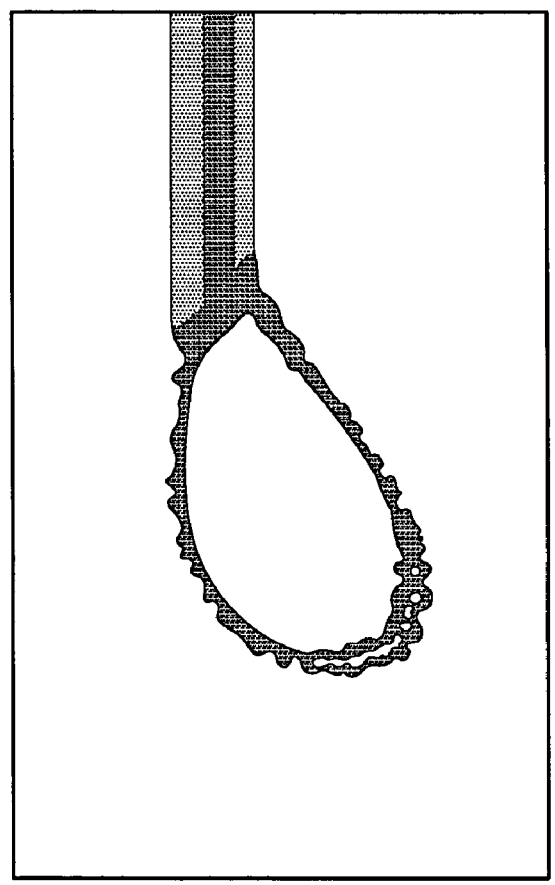
FIG. 3 shows a 10 μm-thick wire loop electrode in saline with cavitation bubbles forming simultaneously along all its length. This effect demonstrates the uniformity in distribution of the electric field along its surface.

The electric field around a sharp exposed blade edge is similar to that on a ring electrode, but the radius of curvature is not limited by mechanical strength anymore. The blade edge can be sharpened much more because the mechanical strength for this structure is provided by the blade. In addition, visibility of this electrode is no longer a problem—the macroscopic blade can be easily observed while its very sharp blade edge might not be well resolved in a conventional surgical microscope. Thus the blade edge of such an electrode can have an edge radius of curvature much smaller than 10 microns. This will strongly reduce the threshold voltage and energy, as well as the penetration depth of the field into the tissue, which in turn leads to a cleaner cut with a smaller zone of damaged tissue. The distribution of electric field along a 5 μm-thick blade edge on a disk electrode is shown in FIG. 1.

The small radius of curvature and low threshold energy make the interaction zone with tissue very shallow, thus fast cutting can be achieved at sufficiently high pulse repetition rates. Cutting tissue by small steps at high repetition rate results in a very smooth action leaving very clean edges of the lesion. For successful insertion of such thin electrode into tissue the layer of insulator on its flat sides (first and second blade surfaces) should be thin—comparable or thinner than the edge radius of curvature.

Providing the blade edge is sharp with nearly uniform edge radius of curvature, the electric field on the blade edge remains uniform, or nearly uniform, even if the planar shape of the electrode is not exactly round. The electric field remains uniform as long as the planar radius of curvature of the blade remains much larger than the edge radius of curvature of the blade edge and the edge radius of curvature is uniform or nearly so. Thus a disk electrode can be deformed into an ellipse or other shape of a blade. Such a blade electrode will preserve a substantially uniform distribution of electric field along the blade edge and can be used for uniform dissection or ablation of tissue with any part on its perimeter. Examples of uniform formation of vapor bubbles and ionization along the blade edge of such an electrode are shown in FIGS. 5A-C.

Optimal Tapering Angle and Material for the Blade Electrode

The field enhancement at the blade edge of the blade electrode depends on the blade tapering angle. The lower the tapering angle, the more effective is the enhancement of the electric field. In addition, a lower blade tapering angle facilitates access to tissue and penetration into it. The threshold energy is reduced by a factor of 2 when the tapering angle changes from 30° to 0°. Thus, for maximal enhancement of the field, as well as for the most convenient access to tissue and penetration into it, the blade tapering angle should preferably be less than 45°, and more preferably less than 30°, and most preferably less than 15°.

To reduce the rate of etching of the blade by hot plasma, the blade electrode should be made of a material capable of withstanding high temperatures. In addition, the material should be hard enough to provide sufficient rigidity when used as a thin blade. Additionally, to reduce the outflow of heat from the treated area via the blade electrode, it should be made of a material with low thermal conductivity. Materials fitting all these characteristics are for example, Tungsten, and more preferably Titanium since its thermal conductivity is 8 times lower.

Pulse Structure for Minimization of Electroporation

One of the mechanisms of tissue damage in electrosurgery is electroporation. This is a direct effect of high electric fields on the membranes of cells. Electroporation results in an increase of the cell permeability and may lead to cell injury or death. To reduce this effect a voltage-balanced or a charge-balanced pair of pulses of opposite polarity instead of a single pulse of one polarity can be applied. This change leads to significant reduction in tissue damage. For example, application of a single pulse of 200 ns duration and 4 kV in amplitude produces electroporation-related damage on the order of 260 µm, while charge-balanced bi-phasic pulses applied to the same electrode at the same amplitude produces only 90 µm of electroporation-related damage (measured on chorioallantoic membrane of chicken embryo using Propidium Iodide staining technique). In addition to its biological advantage, alternating the polarity of the pulses also decreases the erosion rate of the electrode.

In a preferred embodiment, a microblade of 0.2-0.6 mm in length with insulated flat sides and exposed sharp edges serves as an electrode using bi-phasic charge-balanced waveforms with pulse duration varying from 0.1 to 5 us. Retinal dissection has been performed with complete and partial vitrectomy on excised pig eyes and in-vivo rabbit eyes. Results were analyzed clinically and histologically. When no energy is applied the instrument can be used as a vitreoretinal pick to elevate and expose membranes. A train of charge-balanced pulses of alternating polarity can create uniform cutting along the edge of the blade without generation of visible gas in vitreous or fluid medium. Smooth cutting without turbulent flow or other mechanical interference occurs when operating at repetition rates around 100 Hz. Histology and propidium iodide staining of live tissue demonstrate that the collateral damage zone extends 40-80 um from the edge. With different waveforms the blade electrode can also coagulate.

To reduce electroporation, a symmetric AC waveform, (voltage-balanced rather that charge-balanced) can be applied, which results in a damage zone less than 40 µm.

Pulsed Waveform for Neutralization of "Hot Spots".

Uneven distribution of the electric field along the electrode affects its performance not only in the regime of dielectric breakdown in liquid, but also in the regime of evaporation of water. This effect can be neutralized using specially designed pulse waveforms. The energy should be delivered in a burst of pulses in such a way that evaporation of the liquid, leading to vapor bubble growth, first occurs in the areas of high electric field. Providing that the electric field is not sufficiently strong for ionization inside the vapor bubble, the vapor bubble will isolate that part of electrode from the conductive fluid. Hence, evaporation will begin in the surrounding areas having a somewhat weaker electric field. This process should continue until the last area of the electrode is covered by the vapor cavity before the first bubble collapses exposing the electrode in that area. This requirement sets the amplitude and optimal duration of the pulse or burst of pulses. The size of individual bubbles and the number of them can be set by choosing the energy of each pulse in the burst and by number of pulses. An example of such process producing uniform vapor cavity along an electrode with a non-uniform electric field is shown in the sequence of photos of FIG. 6.

In the example of FIG. 6, the wire diameter is 25 microns and the wire length is 1 mm. A single burst of pulses is applied to the wire, having a burst duration of 30 µs, and containing pulses (or minipulses) having a duration of 2.5 µs separated by a pulse interval of 2.5 µs. The pulse voltage is 360 V.

The lifetime of an empty spherical cavity of radius Ro in water (density $p=1000$ kg/m$^3$) and under atmospheric pressure (Po=$10^5$ N/m$^2$) is t=0.91 Ro$(p/Po)^{1/2}$. That means an empty bubble with radius 100 µm will collapse in approximately 10 µs. If the bubble is not empty, i.e. if the vapor pressure inside is significant, the lifetime will increase. No simple estimates for the cavity lifetime is known, but as a first approximation P, which is a difference between the pressure outside and inside the bubble, can replace Po. Thus if the vapor pressure inside is 0.9 Po, then P=0.1 Po, and the lifetime t will increase by a factor of $10^{1/2}$, approximately 3. As the vapor pressure inside the cavity approaches atmospheric pressure the lifetime of the bubble extends to infinity. The amount of vapor inside the cavity depends on the dynamics of the cavity formation. If the bubble is formed as a result of a very fast (as compared to lifetime of the cavitation bubble, which is typically above 10 microseconds) explosion the cavity quickly becomes very cold and is virtually empty. If the bubble is formed by slow (above 10 microseconds) heating and vaporization, the vapor pressure inside will be higher and closer to ambient pressure. These theoretical guidelines can be used to help design waveforms, but some experimentation is likely to be necessary to determine the best waveforms for any particular set of circumstances.

The duration of a burst of pulses is preferably less than 10 ms, and can be less than 1 ms or even less than 0.1 ms, to reduce thermal damage to tissue being cut. The duration of pulses within a burst is preferably between 10 ns and 10 µs. Preferably, adjacent pulses within a burst of pulses have opposite polarity to reduce electroporation damage to tissue. Preferably, bursts are repetitively applied to the electrode such that successive bursts are separated by a burst interval of 1 ms or more.

Figure 7A:
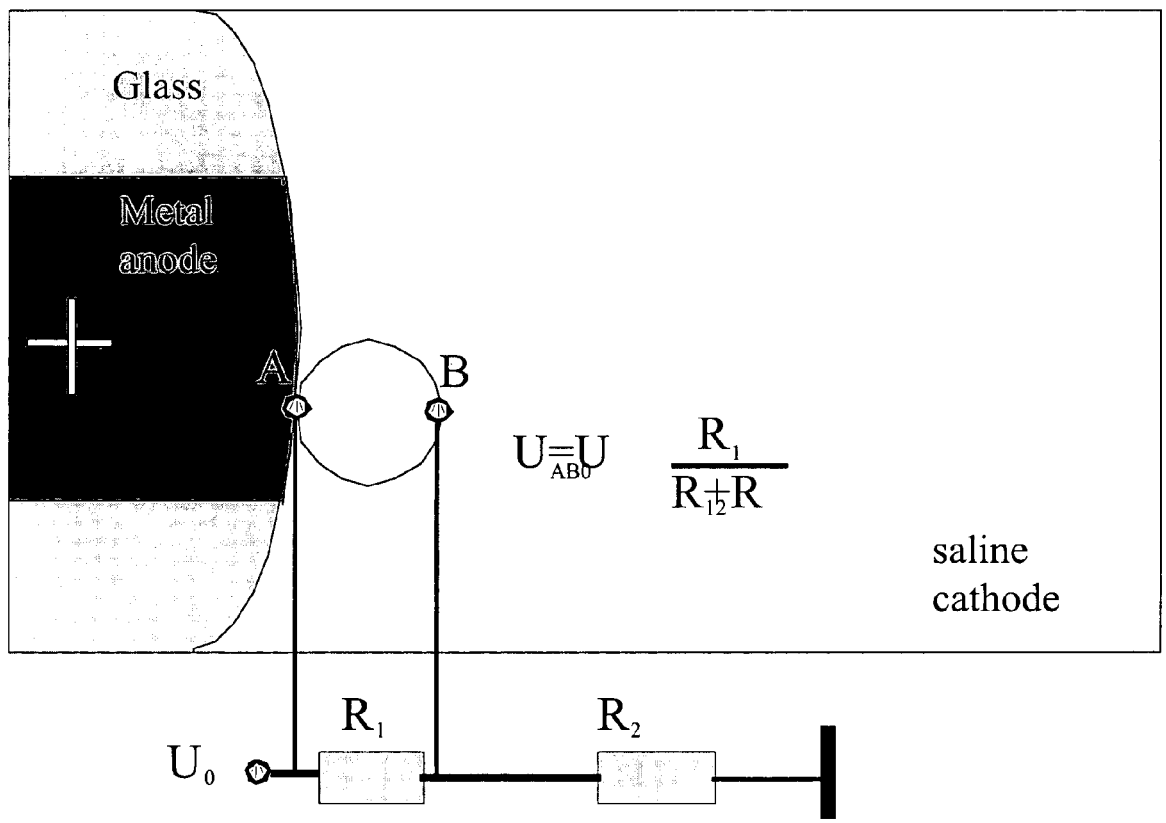
FIGS. 7A-C show a sequence illustrating the initiation of an electric arc.
Figure 7B:
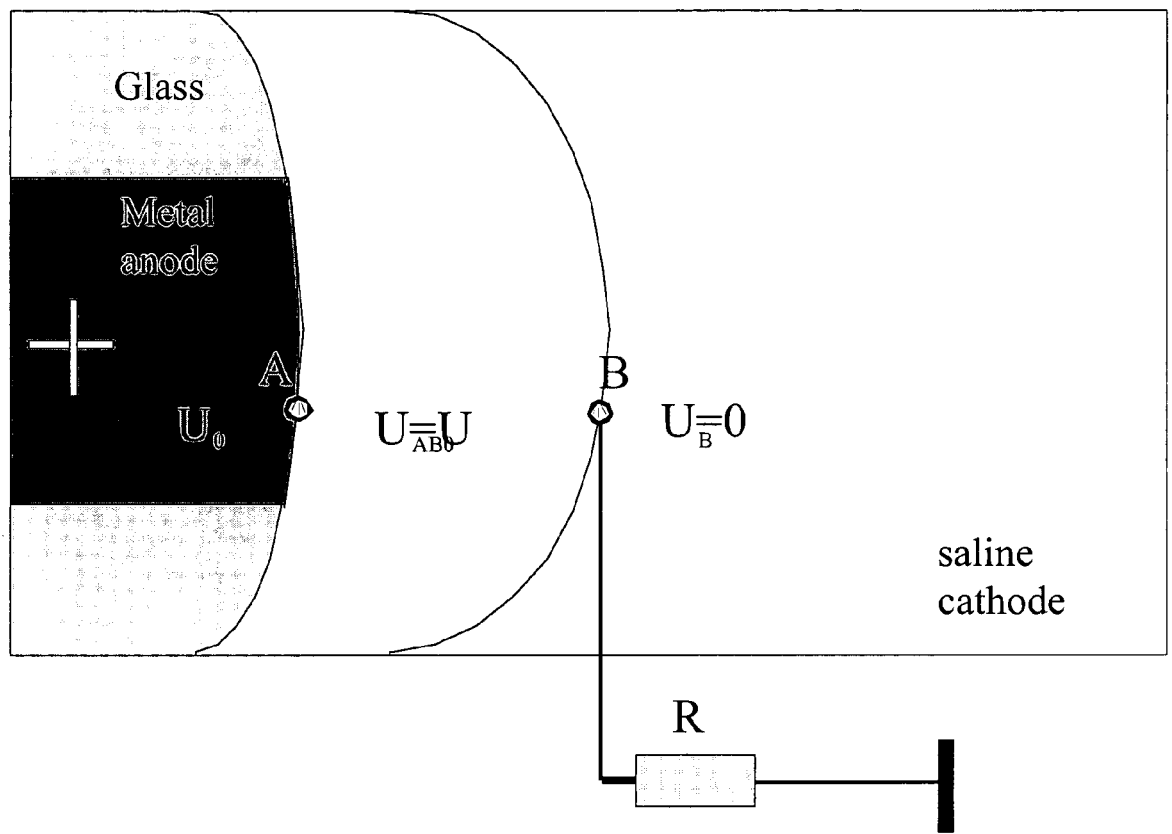
Figure 7C:
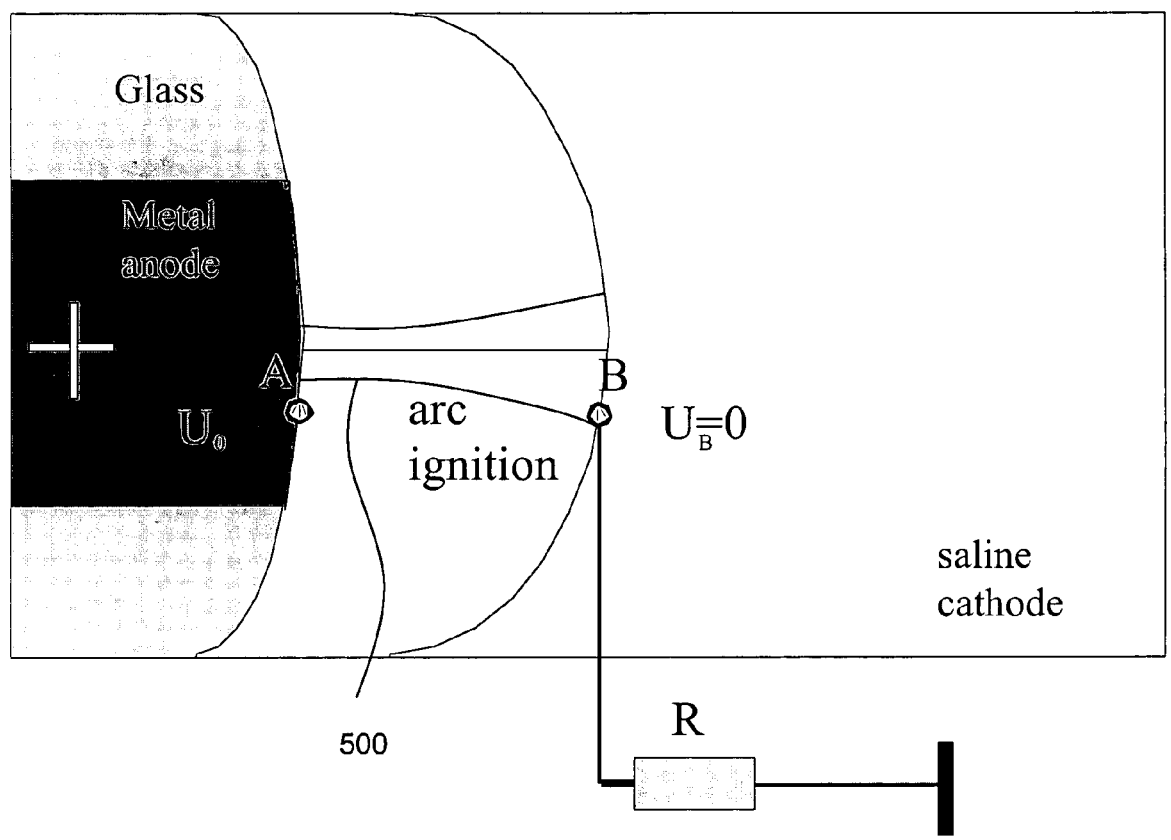

After the vapor cavity covers the entire electrode, with the proper level of the electric field, ionization of the vapor can occur. FIGS. 7A-C illustrate the start of electric discharge in a saline solution. In FIGS. 7A-C, the electrode is a metal anode, glass serves as an insulator, the saline solution is the liquid conductive medium, and a cathode is immersed in the saline solution. FIG. 7A shows the early formation of a vapor cavity in the saline solution. $R_1$ is the resistance from an equipotential through point A to an equipotential through point B. $R_2$ is the electrical resistance from the equipotential through point B to the cathode. $R_2$ is typically much larger than $R_1$, because not all of the anode is blocked by the vapor cavity. Thus, only a small fraction of the anode potential U (i.e., $U R_1/(R_1+R_2)$) is present across the vapor cavity. In other words, the saline alongside the vapor cavity acts as a shunt resistor and thus the voltage drop across a vapor cavity is small until the vapor cavity completely covers the electrode.

FIG. 7B shows the vapor cavity at a later time in which it has grown to completely encompass the anode. Therefore the entire anode potential U is present across the vapor cavity, since current flow is blocked by the vapor cavity. FIG. 7C shows ignition of an electric discharge 500 inside the cavity. When the electrical potential different from A to B exceeds the ionization threshold for the vapor cavity, the gas in the vapor cavity ionizes and current flows from the electrode, across the vapor cavity to the conductive liquid medium. Preferably, the anode voltage U is selected so that U is greater than the ionization threshold for the complete vapor cavity of FIG. 7B, and $U R_1/(R_1+R_2)$ is less than the ionization threshold of the partial vapor cavity of FIG. 7A. Selection of the anode voltage according to this condition ensures that the partial vapor cavity of FIG. 7A does not break down until it has grown to completely cover the anode.

Ideally the bubbles formed during this process grow slowly, on the order of tens of microseconds, so that the maximum velocity associated with bubble growth is below about 10 m/s. Such slow growing bubbles are not as mechanically damaging as cavitation bubbles that have maximum velocities on the order of 100 m/s. In addition, small bubbles are preferred to further minimize mechanical damage at the boundary of the surgical cut.

In applications that involve the cutting of biological tissue, ionization begins and the discharge is predominant in front of tissue, i.e. in the areas where tissue is located closer to electrode than the boundary of the vapor cavity in liquid. Therefore, using this approach, the uniformity of the original electric field is not critical because the tissue will only be exposed to electric current after ionization of the vapor cavity, which will occur substantially uniformly along the vapor cavity. For minimization of electroporation-related damage a burst of pulses should consist of pairs of symmetric bi-phasic or charge-balanced pulses, as described above.

With high electric fields, when ionization of water begins before vaporization, or when vapor cavity is ionized immediately after its formation, the disconnect of electrode from liquid does not occur and thus this process of sequential creation of multiple vapor bubbles along the electrode will not work.

Combination of Sharp Edge with a Burst of Pulses.

A burst of pulses can be applied for vaporization of liquid along a sharp edge of a disk or blade electrode. If a sharp edge is produced along a blade that has a singular point (small planar radius of curvature) at its apex then ordinarily, the advantage of an enhanced electric field associated with the sharp blade edge is tempered by the nonuniformity of the field caused by the apex. However, by using the approach described above for vaporizing the region along the electrode prior to ionizing the vapor bubble the problem of the field non-uniformity can be fixed. The sharp blade edge provides field enhancement that leads to a smaller damage zone and lower threshold energy and is mechanically supported by the thicker part of the insulated blade. The apex with an associated strong field can be neutralized by application of a burst of pulses of optimal duration.

Figure 8A:
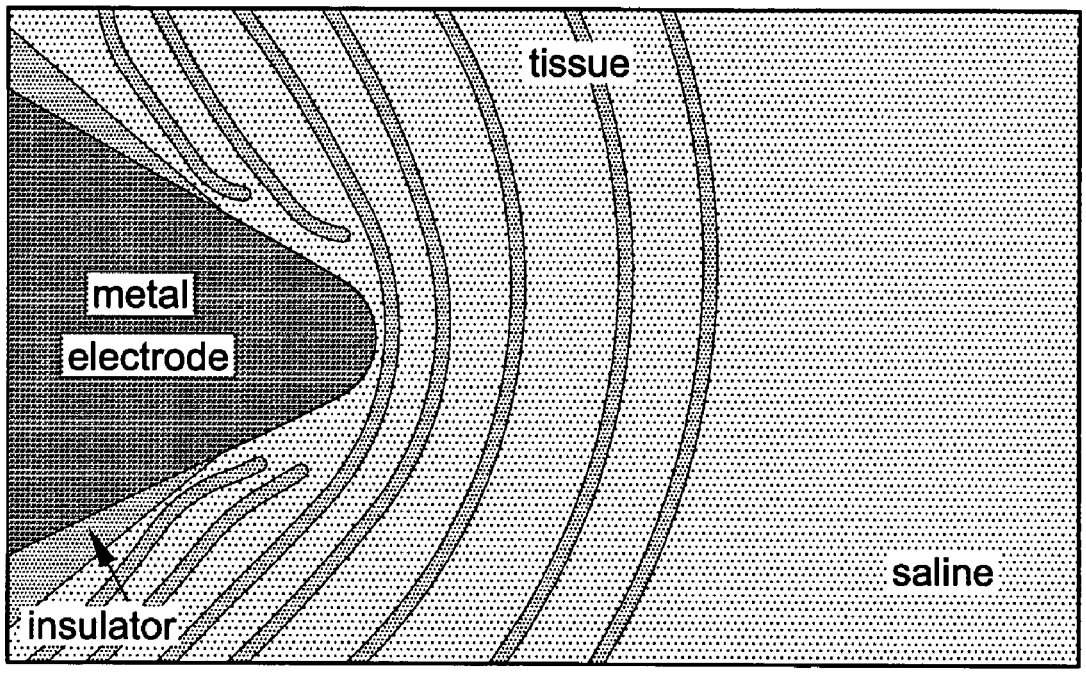
FIGS. 8A-C shown an electrode as a blade edge and biological tissue immersed in saline.
Figure 8B:
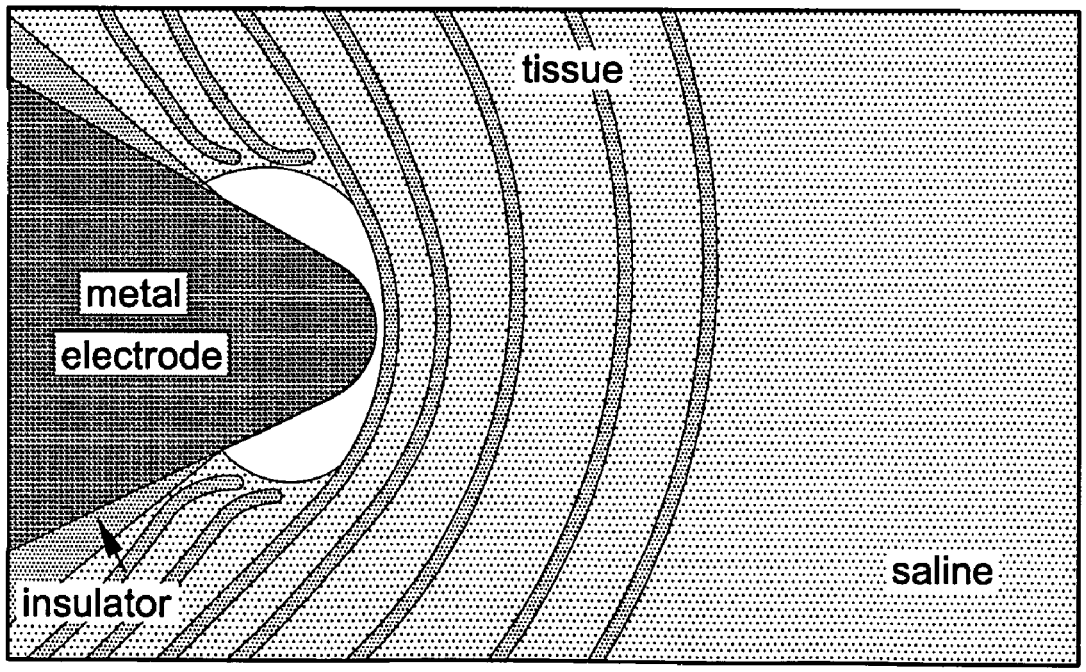
Figure 8C:
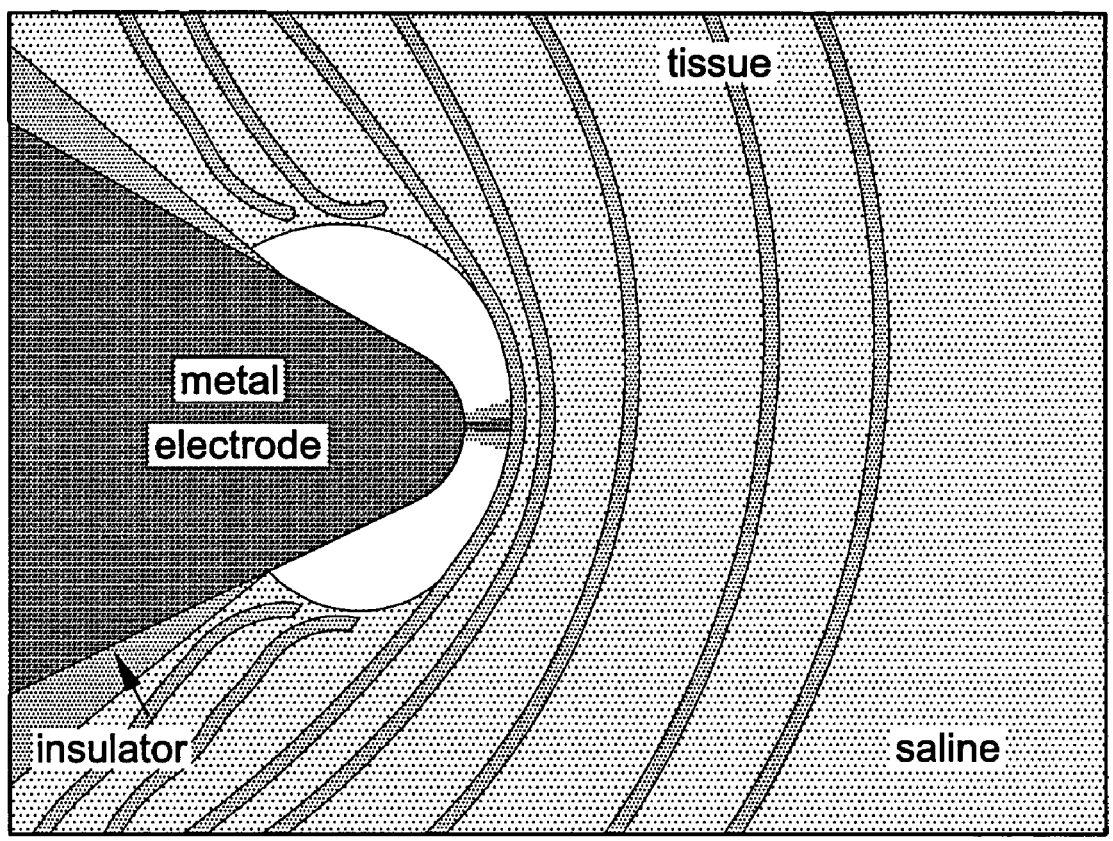

FIGS. 8A-C show the use of a pulsed electric field to first generate a vapor bubble around a sharp blade edge and then produce an electric discharge from the blade to the targeted biological tissue by ionization of the vapor. FIG. 8A shows the blade electrode before the vapor cavity is formed. FIG. 8B shows a vapor cavity forming over the portion of the blade electrode not covered by the insulator. When the electrical potential is high enough, an electric discharge occurs between the blade electrode and the tissue as shown in FIG. 8C. As shown in FIG. 8C, the discharge is concentrated in the region of smallest separation (least resistance) between the electrode and the tissue.

Self-Sharpening of the Edge During "Controlled" Erosion of the Blade Electrode

A thin electrode is rapidly etched during use, especially in the evaporation mode. A sharp blade edge of a blade electrode also is rapidly etched in use. Rounding the edge by etching, i.e., increasing the edge radius of curvature, leads to an increase in the threshold voltage and pulse energy, which in turn, will increase the extent of the collateral damage zone. To prevent this effect a "controlled etching" leading to self-sharpening can be implemented.

Etching is most efficient inside the zone of evaporation (i.e., the vapor bubble). Therefore, the region of most efficient etching can be determined by parameters of the driving waveform, which determine the size of the vapor bubble. Self-sharpening can be achieved by sizing the vapor bubble to include the tapering region near the blade edge. In such a case, efficient etching occurs over the entire tapering region, and the blade edge can be maintained with an approximately constant edge radius of curvature. Optimal width of the etching zone is determined by the thickness of the blade and the desirable tapering angle. For a blade of thickness D outside of the tapering region, blade tapering angle $\alpha$, and edge radius of curvature $r_0$, the tapering region extends a distance $r_0+(D/2-r_0)/\tan(\alpha/2)$ inward from the end of the blade edge. Ideally the vapor bubble should extend at least this far inward from the end of the blade edge. Such a self-sharpening regime keeps the electrode functional for a long time despite the erosion. Alternatively, blade 100 can be slidably mounted between insulators 210 and 220 such that erosion of blade 100 during operation can be compensated by extending a fresh section of blade 100 from between insulators 210 and 220.

Figure 9:
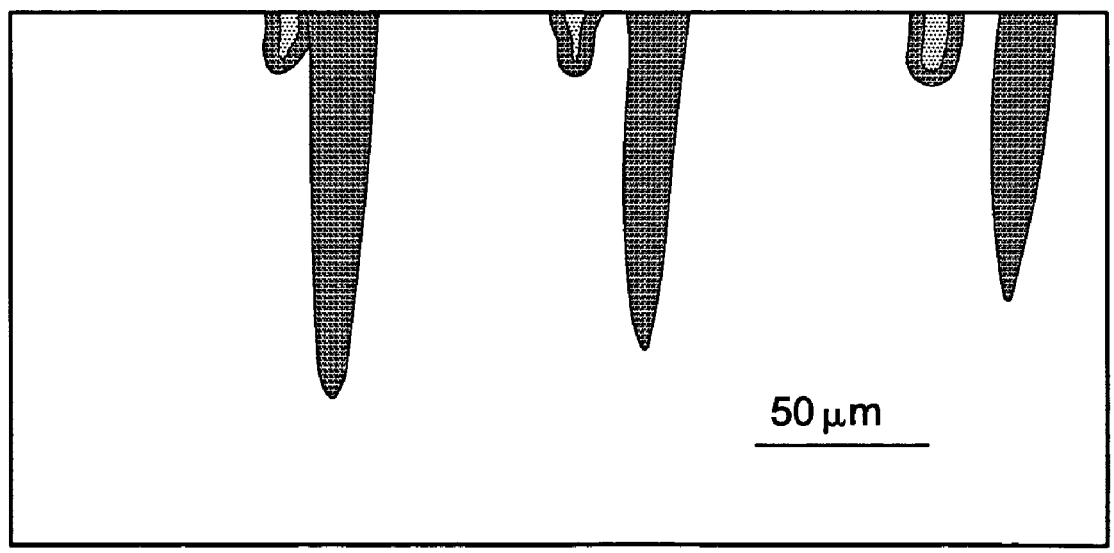
FIG. 9 shows that etching of a 15 μm-thick Tungsten blade by electric discharges at surgical settings leaves the blade edge sharp as it shortens.

Technology for fabrication of such a blade can be simplified by using the electrical discharge itself to remove the insulators from the blade surfaces near the blade edge. Preferably, the blade is milled to achieve an appropriate blade tapering angle either before, or immediately after the blade surfaces are covered with thin layers of insulators. The blade is immersed into a conductive medium and electrical pulses are applied with waveform parameters similar or identical to those appropriate for electrosurgery. The electrical discharge at discontinuities will break and remove the insulator from the active surfaces of the electrode, but in other areas the insulator will remain intact. As the blade edge is etched during use, the insulator in its proximity will be removed as well. FIG. 9 shows the etching of a Tungsten blade by discharges at pulse settings that would be appropriate for surgical cutting. The edge remains sharp as the blade gets shorter.

What is claimed is:

1. An electrosurgical cutting system, comprising:
   a) an electrically conductive blade, said blade having a first surface, a second surface opposite said first surface, and an edge where said first and second surfaces meet, said edge having an edge radius of curvature, wherein a predetermined length of said edge is a cutting portion for cutting biological tissue;
   b) a first insulator on said first surface;
   c) a second insulator on said second surface; and
   d) a source of pulsed electrical energy electrically configured to connect to said blade,
   wherein said source of pulsed electrical energy is configured to apply a plurality of bursts of pulses separated by a burst interval of greater than about 1 ms during which no pulses are present and wherein the duration of the burst of pulses is 1 ms or less;
   wherein said cutting portion has an in-plane radius of curvature that is at least 10 times larger than said edge radius of curvature along the entire length of said cutting portion.

2. The system of claim 1, wherein said edge radius of curvature is less than about 25 microns.

3. The system of claim 2, wherein said edge radius of curvature is less than about 10 microns.

4. The system of claim 3, wherein said edge radius of curvature is less than about 5 microns.

5. The system of claim 4, wherein said edge radius of curvature is less than about 1 micron.

6. The system of claim 1, wherein along said cutting portion said first and second insulators each have a thickness less than said edge radius of curvature.

7. The system of claim 1, wherein along said cutting portion said thickness decreases approximately linearly, within a tapering region, as said first and second surfaces approach said edge thereby to define a blade tapering angle.

8. The system of claim 7, wherein said blade tapering angle is less than 45 degrees.

9. The system of claim 8, wherein said blade tapering angle is less than 30 degrees.

10. The system of claim 9, wherein said blade tapering angle is less than 15 degrees.

11. The system of claim 7, wherein said pulses provided by said source are sufficient to vaporize and ionize a liquid medium present along said cutting portion thereby to form a vapor cavity encompassing said tapering region.

12. The system of claim 7, wherein said pulses provided by said source are sufficient to vaporize and ionize tissue present along said cutting portion thereby to form a vapor cavity encompassing said tapering region.

13. The system of claim 1, wherein said blade comprises Tungsten or Titanium.

14. The system of claim 1, wherein said source of pulsed electrical energy provides pulsed electrical energy with each pulse having opposite electrical polarity to that of the previous pulse.

15. The system of claim 1, wherein said source of pulsed electrical energy provides pulses having a pulse duration between 10 ns and 10 µs.

16. The system of claim 1, wherein each of said bursts of pulses has a duration less than 0.1 ms.

17. The system of claim 1, wherein an energy of each pulse is such that a liquid adjacent to said cutting portion prior to application of the burst of pulses is vaporized.

18. The system of claim 17, wherein a total duration of said burst of pulses is between 5 µs and 500 µs.

19. The system of claim 18, wherein said total duration is between 10 µs and 100 µs.

20. The system of claim 17, wherein any two time-adjacent pulses in said burst of pulses have opposite electrical polarities.

21. The system of claim 1, wherein: said cutting portion is at least 50 µm long; and a strength of an electric field caused by said pulsed electrical energy at said cutting portion varies by no more than 50% along the entire length of said cutting portion.

22. The system of claim 1, wherein said pulses from said source have a duration sufficiently long for generation of a streamer and spark discharge, and sufficiently short to avoid generation of a high current arc discharge.

23. The system of claim 1, wherein said blade is configured and wherein pulses from said source have a voltage such that a vapor cavity formed in a liquid medium adjacent said blade does not ionize until said vapor cavity extends to said first and second insulators.

24. The system of claim 1, wherein said blade and said first and second insulators are configured to be etched together during operation, whereby said edge radius of curvature remains substantially unchanged during operation.

25. The system of claim 1, wherein said blade is slidably mounted between said first and second insulators, whereby said blade can be extended to compensate for erosion of said blade during operation.

26. An electrosurgical cutting system, comprising:
   an electrically conductive blade having a first surface, a second surface opposite the first surface, and an edge where the first and second surfaces meet, wherein a predetermined length of the edge is a cutting portion for cutting biological tissue;
   a first insulated region on said first surface;
   a second insulated region on said second surface; and
   a source of pulsed electrical energy electrically connected to said blade, wherein said source of pulsed electrical energy is configured to apply a plurality of bursts of pulses separated by a burst interval of greater than about 1 ms during which no pulses are present, and wherein the duration of the burst of pulses is 1 ms or less.

27. The system of claim 26, wherein the source of pulsed electrical energy is further configured to apply a plurality of bursts of pulses wherein the pulses are bi-phasic charge-balanced pulses.

28. The system of claim 26, wherein the source of pulsed electrical energy is further configured to apply a plurality of bursts of pulses wherein the pulses have a pulse duration between about 10 ns and 10 µs.

29. The system of claim 26, wherein the source of pulsed electrical energy is further configured to apply a plurality of bursts of pulses wherein the pulses each have a duration between about 0.1 to 5 µs.

* * * * *

UNITED STATES PATENT AND TRADEMARK OFFICE
CERTIFICATE OF CORRECTION

| | | |
|---|---|---|
| PATENT NO. | : 7,357,802 B2 | Page 1 of 1 |
| APPLICATION NO. | : 10/779529 | |
| DATED | : April 15, 2008 | |
| INVENTOR(S) | : Palanker et al. | |

It is certified that error appears in the above-identified patent and that said Letters Patent is hereby corrected as shown below:

In the Specification Under Column 1:

• Please replace Column 1, line no. 15-21 with:

-- FEDERALLY-SPONSORED RESEARCH OR DEVELOPMENT
This invention was made with Government support under contract EY012888 awarded by the National Institutes of Health. The Government has certain rights in this invention. --

Signed and Sealed this
Twenty-third Day of April, 2013

Teresa Stanek Rea
*Acting Director of the United States Patent and Trademark Office*